(12) United States Patent
Thiebaut

(10) Patent No.: US 6,846,951 B1
(45) Date of Patent: Jan. 25, 2005

(54) INTEGRATED PROCESS FOR ACETIC ACID AND METHANOL

(75) Inventor: Daniel Marcel Thiebaut, Lescar (FR)

(73) Assignee: Acetex (Cyprus) Limited, Limassol (CY)

( * ) Notice: Subject to any disclaimer, the term of this patent is extended or adjusted under 35 U.S.C. 154(b) by 0 days.

(21) Appl. No.: 10/605,580

(22) Filed: Oct. 9, 2003

(51) Int. Cl.[7] .................. C07C 27/00; C07C 51/12; C07C 67/36

(52) U.S. Cl. ............. 562/519; 518/700; 518/702; 518/703; 518/704; 560/232

(58) Field of Search ............... 518/700, 702, 518/703, 705; 562/519; 560/232

(56) References Cited

U.S. PATENT DOCUMENTS

| | | | |
|---|---|---|---|
| 1,961,736 A | 6/1934 | Carlin et al. | 562/519 |
| 3,769,329 A | 10/1973 | Paulik et al. | 560/232 |
| 4,888,130 A | 12/1989 | Banquy | 252/373 |
| 4,927,857 A | 5/1990 | McShea et al. | 518/703 |
| 4,999,133 A | 3/1991 | Banquy | 252/373 |
| 5,155,261 A | 10/1992 | Marston et al. | 562/519 |
| 5,180,570 A | 1/1993 | Lee et al. | 423/359 |
| 5,672,743 A | 9/1997 | Garland et al. | 562/519 |
| 5,728,871 A | 3/1998 | Joensen et al. | 562/519 |
| 5,773,642 A | 6/1998 | Denis et al. | 560/232 |
| 5,817,869 A | 10/1998 | Hinnenkamp et al. | 562/519 |
| 5,877,347 A | 3/1999 | Ditzel et al. | 562/519 |
| 5,877,348 A | 3/1999 | Ditzel et al. | 562/519 |
| 5,883,289 A | 3/1999 | Denis et al. | 560/232 |
| 5,883,295 A | 3/1999 | Sunley et al. | 562/519 |
| 6,444,712 B1 | 9/2002 | Janda | 518/706 |
| 6,495,609 B1 | 12/2002 | Searle | 518/700 |

*Primary Examiner*—J. Parsa
(74) *Attorney, Agent, or Firm*—Daniel N. Lundeen; Lundeen & Dickinson, LLP

(57) ABSTRACT

An integrated large capacity, single-train process for making 1,00020,000 MTPD methanol and 3006,000 MTPD acetic acid is disclosed. Syngas 120 is produced by autothermal reforming 118 of natural gas 102 where the feed 112 of the natural gas is supplied with oxygen and CO2 recycle 110 to the autothermal reformer (ATR) 118. A portion (5-50%) of the syngas is fed to CO2 removal 122 to obtain the recycle CO2 and cold box 130 to obtain a hydrogen stream 131 and a CO stream 135. The 50-95% remaining syngas, hydrogen stream 131 and optionally any CO2 from an associated process are fed to methanol synthesis 140, which produces the methanol. The methanol is supplied to an acetic acid unit 136 with the CO 135 to make the acetic acid, which in turn can be supplied to a VAM synthesis unit 148. Oxygen for the ATR and any VAM synthesis can be supplied by a single common air separation unit 116, and utilities such as steam generation can further integrate the process.

36 Claims, 1 Drawing Sheet

INTEGRATED PROCESS FOR ACETIC ACID AND METHANOL

BACKGROUND OF INVENTION

The present invention is directed generally to an improved method for the production of methanol, acetic acid, and other chemicals such as vinyl acetate monomer (VAM) from natural gas. The improved method integrates a carbon monoxide separation plant with a methanol synthesis unit for large-scale methanol and acetic acid manufacture using a single-train process.

Methanol is a major raw chemical material. Major uses of methanol include the production of acetic acid, formaldehyde, and methyl-tert-butyl ether. Worldwide demand for methanol is expected to grow in the next decade as new applications become commercialized such as the conversion of methanol to gas (Mobil MTG Process), the conversion of methanol to light olefins (MTO Process of UOP and Norsk Hydro), the use of methanol for power generation and the use of methanol in fuel-cells. The development of such applications is clearly linked to the methanol production cost. The present invention permits the construction of highly efficient single-train plants for converting natural gas to methanol at low cost in large quantities.

The manufacture of acetic acid from carbon monoxide and methanol using a carbonylation catalyst is well known in the art. Representative references disclosing this and similar processes include U.S. Pat. No. 1,961,736 to Carlin et al (Tennessee Products); U.S. Pat. No. 3,769,329 to Paulik et al (Monsanto); U.S. Pat. No. 5,155,261 to Marston et al (Reilly Industries); U.S. Pat. No. 5,672,743 to Garland et al (BP Chemicals); U.S. Pat. No. 5,728,871 to Joensen et al (Haldor Topsoe); U.S. Pat. No. 5,773,642 to Denis et al (Acetex Chimie); U.S. Pat. No. 5,817,869 to Hinnenkamp et al (Quantum Chemical Corporation); U.S. Pat. No. 5,877,347 and U.S. Pat. No. 5,877,348 to Ditzel et al (BP Chemicals); U.S. Pat. No. 5,883,289 to Denis et al (Acetex Chimie); and U.S. Pat. No. 5,883,295 to Sunley et al (BP Chemicals), each of which is hereby incorporated herein by reference.

The primary raw materials for acetic acid manufacture are typically carbon monoxide and methanol. In the typical acetic acid plant, methanolisimported and carbon monoxide, because of difficulties associated with the transport and storage thereof, is generated in situ, usually by reforming natural gas or another hydrocarbon with steam and/or carbon dioxide. For this reason, attention has recently focused on the construction of integrated plants producing both methanol and acetic acid. A significant expense for new acetic acid production capacity is the capital cost of the equipment necessary for carbon monoxide generation. It would be extremely desirable if this capital cost could be largely eliminated or at least significantly reduced.

The primary raw materials for vinyl acetate monomer manufacture are ethylene, acetic acid and oxygen. Carbon dioxide is produced as an undesirable by product in the reaction and must be removed from the recycled ethylene. A significant expense of new production capacity for syngas, methanol, acetic acid and acetic acid derivatives such as VAM, is the capital cost of the necessary equipment. Other significant expenses include the operating costs, including the cost of raw materials. It would be desirable if these capital and operating costs could be reduced.

For methanol production, it is well established that for a large capacity syngas plant autothermal reforming could be a more economical process leading to synthesis gas, since large capital costs are saved by not constructing large primary reformers or multiple partial oxidation reactors. Nevertheless, the drawback is not being able to have a full usage of all carbon molecules, resulting in the venting of large quantities of CO2, which is undesirable. It is in fact necessary to condition the synthesis gas at the outlet of the autothermal reformer because the stoichiometric number (SN) expressed as $SN=[(H2-CO2)/(CO+CO2)]$ is below 2, usually between 1.7 and 1.9. The goal is to obtain an optimum syngas ratio, which lies in the range of 2.0 to 2.1 for makeup to the methanol synthesis loop. Lee et al disclose in U.S. Pat. No. 5,180,570 an integrated process for making methanol and ammonia in order to approach stoichiometric conditions in the methanol reaction loop. McShea, III et al disclose in U.S. Pat. No. 4,927,857 a catalyst for autothermal reforming and the means to obtain a syngas in stoichiometric proportions by controlling the steam to carbon and oxygen to carbon ratios. Banquy discloses in U.S. Pat. Nos. 4,888,130 and 4,999,133 a process suitable for methanol production on a very large scale where the synthesis gas can be made as close as necessary to the stoichiometric composition required for methanol production, by using the combination of both a primary steam reformer and an autothermal reactor. In an article presented at the 2000 World Methanol Conference in Copenhagen, Denmark (Nov. 8–10, 2000), Streb shows that very large capacity methanol plants require a special process design. Streb suggests that pure autothermal reforming can be used when the feedstock is light natural gas, but emphasizes that in such cases the stoichiometric ratio is less than 2 and may require the need to suppress CO2 conversion.

In U.S. Pat. No. 6,495,609, Searle discloses the recycle of CO2 to a methanol synthesis reactor in the production of ethylene oxide-from ethylene. In U.S. Pat. No. 6,444,712, Janda discloses the recycle of CO2 back to either the reformer or the methanol synthesis loops to control the SN between 1.6 and 2.1. Both Searle and Janda demonstrate the manipulation of the SN through the use of steam and partial oxidation reformers. Generally, steam reformers generate syngas with an SN greater than 2.8, while partial oxidation reformers produce syngas having an SN between 1.4 and 2.1.

SUMMARY OF INVENTION

It has now been discovered that a typical plant employing an autothermal reformer can be adapted for methanol production by integrating an acetic acid plant that consumes carbon monoxide for carbonylating an ad hoc stream of methanol. The carbon monoxide is separated from a portion of the reformer effluent with CO2 recovery recycled to the reformer and hydrogen returned to the methanol synthesis. The amount of reformer effluent from which the CO is recovered is balanced to result in the desired SN for the makeup syngas to the methanol loop.

The present invention combines a methanol synthesis process with an acetic acid process. The invention takes advantage of having a carbon monoxide separation plant upstream the methanol reactor, to adjust the remaining syngas SN between 2.0 and 2.1 and more preferably, close to 2.05. The invention provides a method that produces methanol, acetic acid and optionally vinyl acetate monomer or the like. It also involves the discovery that the large capital costs can be reduced through a specific manner of integrating the manufacturing processes of these compounds into one integrated, single-train process.

The present invention in one embodiment provides a method for manufacturing methanol and acetic acid, characterized by the integrated steps of: autothermally reforming a hydrocarbon stream, such as natural gas, with oxygen, steam and carbon dioxide to produce a syngas stream; separating a portion comprising from 5 to less than 50 percent, preferably from 5 to 40 percent, more preferably from 10 to 30 percent, and even more preferably from 15 to 25 percent of the syngas stream into a carbon dioxide-rich stream, a hydrogen-rich stream, a carbon monoxide-rich stream and a methane-rich stream; optionally using the methane-rich stream as fuel; recycling the carbon dioxide-rich stream to the autothermal reforming step; compressing a remaining portion comprising between at least 50 and up to 95 percent, preferably between 60 to 95 percent, more preferably between 70 and 90 percent, and even more preferably from 75 to 85 percent of the syngas stream, with at least a portion of the hydrogen-rich stream to supply a makeup stream having an SN between 2.0 and 2.1, preferably between 2.04 and 2.06, to a methanol synthesis loop to obtain a methanol product; and synthesizing acetic acid from at least a portion of the methanol product and the carbon monoxide-rich stream.

The method can also include combining a hydrogen-containing stream with a natural gas feed containing higher hydrocarbons to form a hydrogen containing feed stream, and contacting the feed stream with a hydrogenation catalyst at hydrogenation temperatures to produce a pretreated stream lean in higher hydrocarbons.

The method can include supplying a purge gas stream from the methanol synthesis step to the prereformer, to fuel and/or to the separating step. In the later case inerts are purged from the system in the methane-rich stream as a tail gas following CO and hydrogen recovery, e.g. from a cold box.

The method preferably produces methanol at from 1,000 to 20,0000 metric tons/day, and acetic acid at from 300 to 6,000 metric tons/day, using a single-train autothermal reformer.

The method can also include supplying an imported carbon dioxide stream and/or a carbon dioxide stream from an associated process to the methanol synthesis loop. For example, the associated process uses the acetic acid as a reactant, uses the methanol product as a reactant, shares oxygen from a common air separation unit, shares common utilities, or a combination thereof. At least a portion of the acetic acid produced can be supplied to a vinyl acetate monomer (VAM) synthesis loop in the associated process for reaction with ethylene and oxygen to produce VAM. A carbon dioxide-rich stream from the VAM synthesis loop can be imported to the methanol synthesis loop.

The feed stream can also be pretreated by hydrogenation to allow a lower steam to carbon ratio to be employed while avoiding soot formation in the autothermal reformer, and the corresponding process facility. In this method, a hydrogen-rich stream is added to a feed gas stream containing higher hydrocarbons (2 or more carbon atoms), the resulting mixture is contacted with a hydrogenation catalyst at a hydrogenation temperature, and the hydrogenated mixture is fed to an autothermal reformer with steam and oxygen to form syngas. The hydrogen-rich stream is preferably a purge gas or fraction thereof from a methanol synthesis loop receiving syngas or a portion or fraction thereof. The hydrogen-rich stream is preferably added at a rate to provide at least a stoichiometric amount of hydrogen for hydrogenation of the higher hydrocarbons to methane. The hydrogenation temperature can preferably be from 300° C. to 550° C. The process facility in this embodiment includes a feed gas comprising higher hydrocarbons; a pre-hydrogenation reactor comprising hydrogenation catalyst for converting the higher hydrocarbons to form a higher-hydrocarbon-lean stream (base metals such as platinum, palladium, cobalt, molybdenum, nickel or tungsten, supported on alumina or a zeolite are commonly used as catalyst); an autothermal reformer for reacting the higher-hydrocarbon-lean stream with steam and oxygen to form a syngas stream; a methanol synthesis loop for reacting hydrogen and carbon monoxide from the syngas stream to form methanol; a purge gas stream from the methanol synthesis loop; and a line for supplying a portion of the purge gas stream to the pre-hydrogenation reactor.

Because the reaction is exothermic, the hydrogenation process can be done in one or several reactors, with intermediate coolers if necessary. This hydrogenation step is particularly well adapted for use with autothermal reformers having a low steam to carbon ratio in the feed.

DETAILED DESCRIPTION

Figure 1:
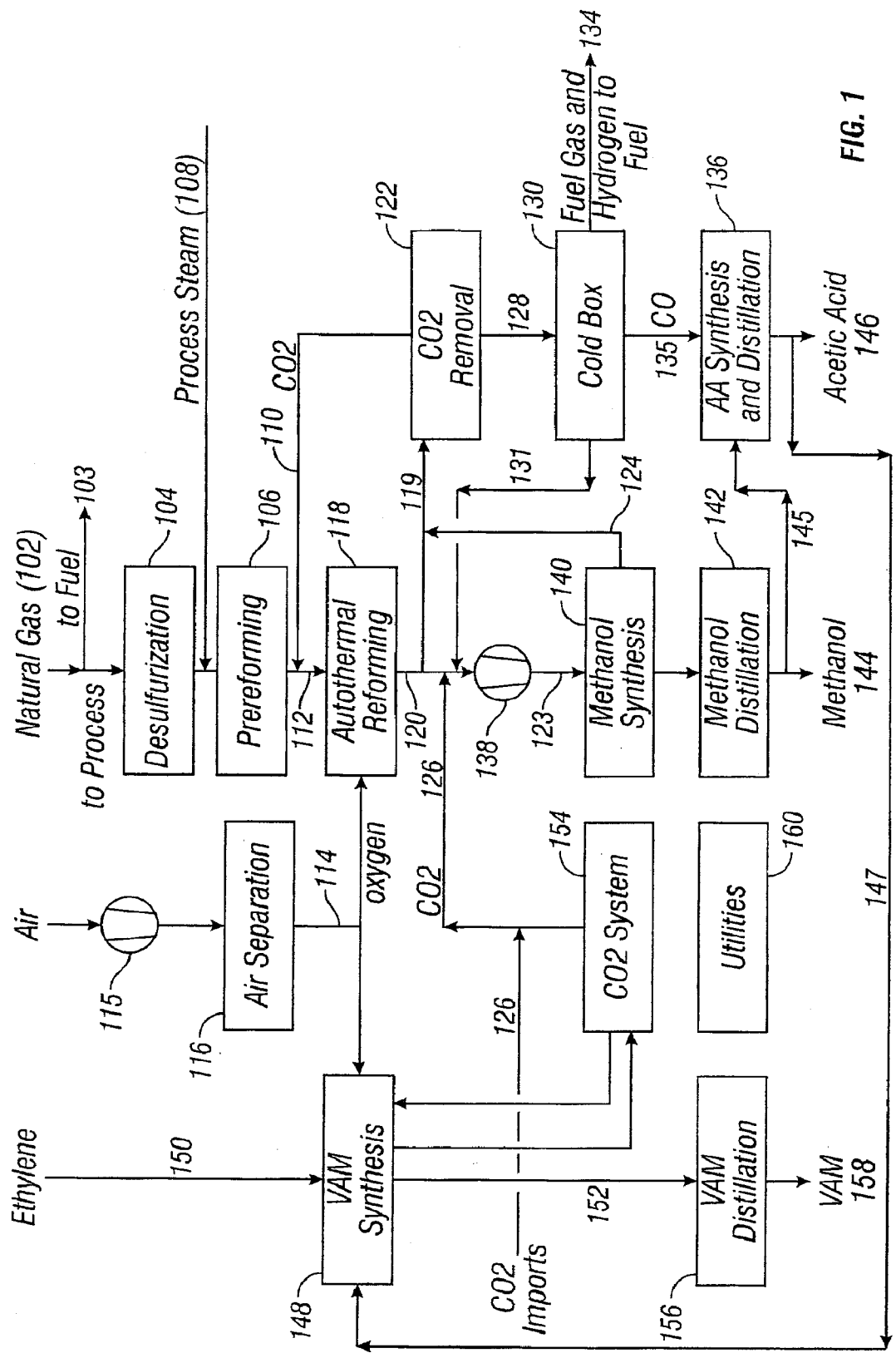
FIG. 1 is a simplified block flow diagram of an embodiment according to the present invention of a process for making methanol, acetic acid and vinyl acetate monomer, employing an autothermal reformer for the production of syngas.

The plant for the process can be a new plant, but it could also be a retrofit of an existing methanol, acetic acid and/or VAM plant.

Natural gas 102 is provided as both fuel 103 for the plant as well as gas feed for the synthesis. The natural gas combined with an hydrogen-rich stream is supplied to a conventional desulfurization unit 104 and optionally fed to an adiabatic, catalytic prereformer 106 with steam 108. The prereformer can be useful in reducing soot formation in the downstream ATR where the natural gas contains appreciable C2 and higher hydrocarbons. Air is compressed in compressor 115 and fed to an air separation unit (ASU) 116, which is operated in a conventional manner to obtain the oxygen stream 114. The effluent 112 is fed with oxygen 114 obtained from ASU 116, and a recycled CO2-rich stream 110. The mixture of preformed natural gas, carbon dioxide, and steam if necessary, is introduced to autothermal reformer 118 with the oxygen for catalytic reforming using conventional autothermal reforming equipment and catalyst systems to produce syngas stream 120. The syngas stream 120 is conventionally cooled and freed from condensed liquid water.

A portion of the syngas stream 120 is fed to CO2 removal unit 122 via line 119 to produce the CO2 recycle stream 110, previously mentioned. The amount of syngas directed to stream 119 depends primarily on the amount of CO needed for acetic acid synthesis, but comprises at least 5 percent of stream 120 up to 50 percent, preferably from 5 to 40 percent, more preferably from 10 to 30 percent and even more preferably from 15 to 25 percent of the stream. The methanol and acetic acid production should be matched to take full advantage of the H2, CO, and CO2 produced, preferably from 1,000 to 20,000 metric tons/day methanol and from 300 to 6,000 metric tons/day acetic acid. For a specified methanol production, there is an optimal acetic acid production where the syngas number matches the SN target, e.g. 2.05. If more acetic acid than this is produced, relative to the methanol produced, there will be more hydrogen produced than needed for methanol synthesis, e.g. the SN may be too high or excessive hydrogen sent to fuel. Of course, if imported carbon dioxide is available, the extra hydrogen can be balanced to some extent. If less acetic acid is produced, there will be insufficient hydrogen, e.g. the SN will be too low. If the total production of methanol and acetic acid is increased, the technological capacity limits of one ASU can be exceeded, requiring the excessive capital cost of a second ASU. On the other hand, if the total production is reduced, there is a loss of the economy of scale and the capital costs per unit of production will increase.

The CO2 removal unit 122 can use conventional CO2 removal processes and equipment to remove the CO2, e.g. solvent absorption and stripping. All or a portion of the methanol synthesis loop purge gas stream 124, can also, if desired, be fed to the CO2 removal unit via line 119.

The CO2 removal unit produces a CO2-rich stream 110 and a mixed CO/H2 stream 128 essentially free of CO2. The CO2-rich stream 110 is introduced to the syngas stream 112 upstream the autothermal reformer 118. All or a portion of CO2 imported from the VAM synthesis process, or from any another associated process, or a combination thereof via line 126 can be mixed with the CO2-rich stream from 122 and sent via line 110 upstream the autothermal reformer 118.

Separation unit 130, which preferably comprises molecular sieves and a conventional cold box, splits the stream 128 into at least a CO-rich stream 135 and an H2 rich stream 131, but can also include minor amounts of one or more residual or tail gas streams of mixed hydrogen, methane and CO used as fuel or exported via line 134. The separation unit 130 can be, for example, a partial condensation box with two columns. The CO-rich stream 135 can be supplied to the acetic acid synthesis unit 136, as discussed in more detail below. If the natural gas feed has too high a nitrogen content, a column for nitrogen removal may be added to deliver CO with a purity grater than 97% to the acetic acid synthesis.

The remaining syngas from line 120, CO2 from stream 126, and hydrogen from stream 131, are compressed to methanol synthesis pressure in compressor 138, and fed as makeup stream 123 to the methanol synthesis unit 140 employing a methanol synthesis loop and catalytic methanol synthesis reactors well known in the art. Purge gas stream 124 from the synthesis unit 140 can be recycled to the CO2 removal unit 122, as described above. As is well known, the purge gas stream 124 is necessary to prevent the buildup of inerts such as argon and methane in the methanol synthesis loop. Processing the purge gas in the CO2 removal unit 122 and the cold box 130 has the advantage of recycling the CO2, CO and hydrogen from the purge gas, while rejecting the inerts to the residual stream 134. Methanol product can be purified by a distillation. unit 142 or other conventional process. Purified methanol is exported as product via line 144, or a portion may be supplied to the acetic acid synthesis unit 136 via line 145.

The acetic acid synthesis unit 136 employs conventional acetic acid manufacturing equipment and methodology well known and/or commercially available to those skilled in the art to form acetic acid from CO via stream 135 and methanol via stream 145, such as, for example, from one or more of the acetic acid manufacturing patents mentioned above. For example, a conventional BP/Monsanto process can be employed, or an improved BP/Monsanto process employing BP-Cativa technology (iridium catalyst), Celanese low water technology (rhodium-lithium acetate catalyst), Millennium low water technology (rhodium-phosphorus oxide catalyst) and/or dual process methanol carbonylation-methyl formate isomerization. The reaction generally comprises reacting methanol, methyl formate, or a combination thereof in the presence of a reaction mixture comprising carbon monoxide, water, a solvent and a catalyst system comprising at least one halogenated promoter and at least one compound of rhodium, iridium, or a combination thereof. The reaction mixture preferably has a water content up to 20 weight percent. Where the reaction comprises simple carbonylation, the water content in the reaction mixture is preferably from about 14 to about 15 weight percent. Where the reaction comprises low-water carbonylation, the water content in the reaction mixture is preferably from about 2 to about 8 weight percent. Where the reaction comprises methyl formate isomerization or a combination of isomerization and methanol carbonylation, the reaction mixture preferably contains a nonzero quantity of water up to 2 weight percent. The reaction is typically continuous. An acetic acid product is obtained via line 146.

If desired, a portion of the acetic acid from line 146 can be fed via line 147 to an associated process that produces CO2 as a by product, such as conventional vinyl acetate monomer (VAM) synthesis unit 148. The acetic acid is reacted with ethylene via line 150 and at least a portion of the oxygen 114 from the air separation unit 116. A liquid product stream 152 is processed in conventional VAM distillation unit 156 to produce essentially pure (commercial specification) VAM via line 158. Carbon dioxide by-product from the VAM synthesis is separated from the reactor effluent gases via conventional CO2 removal system 154 and recycled to the methanol synthesis loop via line 126. The oxygen in line 114 can be obtained, for example, using a conventional (preferably cryogenic) air separation unit 116 producing the amount of oxygen needed to supply both the VAM synthesis unit 148 and the autothermal reformer 118.

VAM production is mainly achieved by the acetoxylation of ethylene according to the reaction:

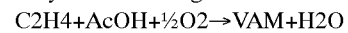
C2H4+AcOH+½O2→VAM+H2O

The main by-product is CO2 formed by the reaction:

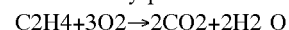
C2H4+3O2→2CO2+2H2 O

Selectivity for this process yields approximately 7–8% CO2 by mass. A VAM plant producing approximately 100,000 metric tons per year (MTY) requires approximately 35,000 MTY of ethylene and produces between 5,000 and 10,000 MTY of CO2.

Utilities 160, which typically include the steam system, cooling water, compressed air and the like, are supplied within the integrated system as needed, with the further concomitant advantage of economies of scale incidental to larger utility supply systems for the integrated plant relative to each individual unit thereof. Notably, steam generated by waste heat recovery from ATR 118, as well as from the methanol synthesis unit 140, the acetic acid synthesis unit 136 and/or VAM synthesis unit 148 or any other associated integrated unit, can be used to drive or supply steam to the boiler feed water pump, sweet cooling water pump, sea cooling water pump, natural gas compressor, ASU compressor 115, preformer 106, ATR 118, CO2 removal unit 122, makeup compressor 138, methanol syngas recycle compressor, and the like. In contrast to the typical situation where excess steam is produced by steam reforming, there is preferably no steam exported by the integrated system of the present invention. Where needed, an auxiliary boiler can supply additional steam for the process.

EXAMPLE 1

In this example, flow rates, compositions and other properties are approximated to two significant figures unless otherwise noted; flow rates are in normal cubic meters per hour (Nm3/h) and compositions in mole percent, unless otherwise noted. A process according to the embodiment of the invention for a MeOH/AcOH/VAM process shown in FIG. 1 is designed for a plant producing 5,088 metric tons per day (MTPD) methanol and 20,000 Nm3/h CO for acetic acid synthesis. Natural gas 102 is provided at 190,000 Nm3/h as both fuel 103 for the plant (16,000 Nm3/h) as well as process feed gas (175,000 Nm3/h). The natural gas, having a composition of approximately 89.5% methane, 5% ethane, 1.0% propane, 0.5% butane and heavier hydrocarbons, and 4.0% nitrogen, is combined with a portion of the methanol synthesis loop gas purge (8,300 Nm3/h) and supplied to desulfurization unit 104 to remove any sulfur compounds. The combined stream (183,000 Nm3/h) is desulfurized and then combined with steam (180,000 Nm3/h) for prereforming 106 to obtain 380,000 Nm3/h effluent comprising 1.8% nitrogen, 2.3% CO2, less than 0.1% CO, 6% hydrogen, less than 44% steam, and 46% methane.

The desulfurized natural gas effluent (380,000 Nm3/h) in line 112 is fed to the autothermal reformer 118 with 12,000 Nm3/h recycle CO2 via line 110 comprising 98% CO2 and less than 1% each of CO, hydrogen, water vapor, and methane. The ATR 118 consumes an additional 110,000 Nm3/h steam and 99,000 Nm3/h oxygen via line 114, comprising 0.5% argon, producing 580,000 Nm3/h of effluent (following drying) comprising 9% CO2, 23% CO, 65% hydrogen, 1.2% nitrogen, and less than 1% each of water vapor, methane and argon.

A 125,000 Nm3/h portion of the dried effluent (approximately 22% of the stream) from the ATR 118 is supplied to the CO2 removal unit 122. The CO2-rich stream 110 is described above, and the CO2-lean stream comprises 112,000 Nm3/h of gas with a composition of 25% CO, 72% hydrogen, 1% of methane, 1.3% of nitrogen and less than 1% each of argon and methane, which is supplied to the cold box 130.

The cold box 130, a condensation cold box with nitrogen removal, produces a 20,000 Nm3/h stream 131 of 98% CO with less than 1% each of hydrogen, nitrogen, argon and methane; a tail gas stream 134 of 4,700 Nm3/h comprising 26% CO, 36% hydrogen, 23% methane, 15% nitrogen, and less than 1% of argon; and an 87,000 Nm3/h stream 128 comprising 90% hydrogen, 9% CO and less than 1% each of nitrogen, argon and methane.

The remainder of stream 120 along with the major portion of stream 131, are compressed to stream 123 to supply 541,000 Nm3/h of makeup gas comprising 69% hydrogen, 21% CO, 8.4% CO2, 1.0% methane, and less than 1% each of water vapor, nitrogen and argon (SN=2.04), to the methanol synthesis unit 140. The unit 140 produces the purge gas stream 124 as previously mentioned; 248,000 kg/h of crude methanol containing 17.5% water, 1.6% CO2, and less than 1% each of CO, hydrogen, argon and methane; and 212,000 kg/h of commercially pure methanol in streams 144 and 145.

Stream 145 supplies 26,000 kg/h of methanol to the acetic acid synthesis unit 136 which is reacted in the classical Monsanto process with the CO via stream 135 to obtain 49,000 kg/h of commercial glacial acetic acid after distillation, at a purity greater than 99.85 wt %.

A portion of the acetic acid from line 146 is fed at 22,000 kg/h to VAM synthesis unit 148 where it is reacted with 10,000 Nm3/h of polymerization grade ethylene, comprising more than 99.9% ethylene and less than 0.1% of impurities, via line 150, and 6,000 Nm3/h oxygen from air separation unit 116 to obtain 31,000 kg/h commercial VAM product stream 152, with a purity greater than 99.9 wt %. VAM production is mainly achieved by the acetoxylation of ethylene. A CO2 stream comprising more than 98% CO2 is produced at 1,400 Nm3/h and recovered from CO2 removal system 154.

In this example, the CO2 stream is not recycled to the methanol synthesis loop via line 126. If necessary or desired, additional CO2 could alternatively or additionally be imported via line 127 to supplement the total CO2 needed via line 126.

The steam balance for this exemplary process requires a high-pressure steam auxiliary boiler producing 180 MT/h steam at 101 bar and 500° C. The carbon efficiency exclusive of acetic acid synthesis 136 and VAM synthesis 148 (including VAM distillation 156 and CO2 system 154) is approximately 82%.

EXAMPLE 2

In this example, the conditions are the same as the previous example with the exception that the CO2 from the VAM process is recycled to the methanol synthesis via line 126. In order to adjust the SN to the optimal value of 2.05, 131,000 Nm3/h of the effluent from the ATR 118 is now sent to the CO2 removal 122 and the CO separation 130, and the hydrogen-rich stream from the cold box 130 is sent to the methanol synthesis loop via 131. Alternatively, because the entire hydrogen-rich stream is delivered to the methanol synthesis loop in this example, a pressure swing adsorption (PSA) unit could be employed to deliver a purified hydrogen stream. A portion of the purified hydrogen-rich stream could optionally be introduced to the methanol synthesis to adjust the SN, in case of normal operating fluctuations.

The CO production on is then increased to 21,000 Nm3/h and the acetic acid production is increased by 5% to 51 MT/h, while the methanol production is now 5,105 MTPD.

The inventions are described above in reference to specific embodiments for illustrative and non-limiting purposes. Various modifications and variations will occur to the skilled artisan in view thereof. It is intended that all such modifications and variations within the scope and spirit of the appended claims be embraced thereby.

What is claimed is:

1. A method for manufacturing methanol and acetic acid, characterized by the integrated steps of:

autothermally reforming a hydrocarbon stream with oxygen, steam and carbon dioxide to produce a syngas stream;

separating a portion of the syngas stream into a carbon dioxide-rich stream, a hydrogen-rich stream, and a carbon monoxide-rich stream;

recycling the carbon dioxide-rich stream to the autothermal reforming step;

compressing a remaining portion of the syngas stream, with at least a portion of the hydrogen-rich stream to supply a makeup stream having a SN between 2.0 and 2.1 to a methanol synthesis loop to obtain a methanol product;

synthesizing acetic acid from at least a portion of the methanol product and the carbon monoxide-rich stream.

2. The method of claim 1, further comprising:

combining a hydrogen-containing stream with a natural gas feed containing higher hydrocarbons to form a hydrogen containing feed stream; and contacting said feed stream with a hydrogenation catalyst at hydrogenation temperatures to produce a pretreated stream lean in higher hydrocarbons.

3. The method of claim 1, wherein the portion of the syngas stream separated into the carbon dioxide-rich, the hydrogen-rich and carbon monoxide-rich streams comprises from 5 to 50 percent of the syngas stream, and the remaining portion comprises from 50 to 95 percent of the syngas stream.

4. The method of claim 1, wherein the portion of the syngas stream separated into the carbon dioxide-rich, the hydrogen-rich and carbon monoxide-rich streams comprises from 5 to 40 percent of the syngas stream, and the remaining portion comprises from 60 to 95 percent of the syngas stream.

5. The method of claim 1, wherein the portion of the syngas stream separated into the carbon dioxide-rich, the hydrogen-rich and carbon monoxide-rich streams comprises from 10 to 30 percent of the syngas stream, and the remaining portion comprises from 70 to 90 percent of the syngas stream.

6. The method of claim 1, wherein the portion of the syngas stream separated into the carbon dioxide-rich, the hydrogen-rich and carbon monoxide-rich streams comprises from 15 to 25 percent of the syngas stream, and the remaining portion comprises from 75 to 85 percent of the syngas stream.

7. The method of claim 1 wherein the SN is between 2.04 and 2.06.

8. The method of claim 1, further comprising supplying a purge gas stream from the methanol synthesis loop to fuel, the separation step, the prereforming step, or a combination thereof.

9. The method of claim 1, further comprising supplying the portion of the hydrogen-rich stream from the separating step to the prereformer.

10. The method of claim 1, wherein the purge gas stream from the methanol synthesis is purified in a PSA unit to produced a purified hydrogen stream.

11. The method of claim 10, wherein a portion of the purified hydrogen stream is introduced to the methanol synthesis loop to adjust the SN of the feed gas stream.

12. The method of claim 1, wherein the methanol produced is between 1,000 and 20,000 metric tons/day.

13. The method of claim 1, wherein the acetic acid produced is between 300 and 6,000 metric tons/day.

14. The method of claim 1, wherein the reforming step uses a single train autothermal reformer.

15. The method of claim 1, further comprising supplying an imported carbon dioxide stream to the methanol synthesis loop.

16. The method of claim 15, wherein the imported carbon dioxide stream is supplied from an associated process to the methanol synthesis loop.

17. The method of claim 16, wherein the associated process uses the acetic acid as a reactant, uses the methanol product as a reactant, shares oxygen from a common air separation unit, shares common utilities, or a combination thereof.

18. The method of claim 17, further comprising:
providing at least a portion of the acetic acid produced to a vinyl acetate monomer (VAM) synthesis loop in the associated process;
combining the portion of the acetic acid with an ethylene source and oxygen to produce vinyl acetate monomer.

19. The method of claim 18, wherein a CO2-rich stream is imported to the methanol synthesis loop from the VAM synthesis loop.

20. The method of claim 1, wherein the separating step produces a tail gas stream rich in inerts.

21. A method for manufacturing methanol and acetic acid, characterized by the integrated steps of:
combining a hydrogen-containing stream with a natural gas feed containing higher hydrocarbons to form a hydrogen containing feed steam;
contacting the hydrogen-containing feed stream with a hydrogenation catalyst at hydrogenation temperatures to produce a pretreated stream lean in higher hydrocarbons;
autothermally reforming the pretreated stream with oxygen, steam, and carbon dioxide to produce a syngas stream;
separating a portion of the syngas stream into a carbon dioxide-rich stream, a hydrogen-rich stream, and a carbon monoxide-rich stream;
recycling the carbon dioxide-rich stream to the autothermal reforming step;
compressing a remaining portion of the syngas stream, with at least a portion of the hydrogen-rich stream to supply a makeup stream having a SN between 2.0 and 2.1 to a methanol synthesis loop to obtain a methanol product;
recovering a purge gas stream from the methanol synthesis loop;
synthesizing acetic acid from at least a portion of the methanol product and the carbon monoxide-rich stream.

22. The method of claim 21, wherein the portion of the syngas stream separated into the carbon dioxide-rich, the hydrogen-rich and carbon monoxide-rich streams comprises from 5 to 50 percent of the syngas stream, and the remaining portion comprises from 50 to 95 percent of the syngas stream.

23. The method of claim 21, wherein the portion of the syngas stream separated into the carbon dioxide-rich, the hydrogen-rich and carbon monoxide-rich streams comprises from 5 to 40 percent of the syngas stream, and the remaining portion comprises from 60 to 95 percent of the syngas stream.

24. The method of claim 21, wherein the portion of the syngas stream separated into the carbon dioxide-rich, the hydrogen-rich and carbon monoxide-rich streams comprises from 10 to 30 percent of the syngas stream, and the remaining portion comprises from 70 to 90 percent of the syngas stream.

25. The method of claim 21, wherein the portion of the syngas stream separated into the carbon dioxide-rich, the hydrogen-rich and carbon monoxide-rich streams comprises from 15 to 25 percent of the syngas stream, and the remaining portion comprises from 75 to 15 percent of the syngas stream.

26. The method of claim 21, further comprising supplying the purge gas stream from the methanol synthesis loop to fuel, the separation step, the prereforming step, or a combination thereof.

27. The method of claim 21, further comprising supplying a portion of the hydrogen-rich stream from the separating step to the prereforming step.

28. The method of claim 21, wherein the purge gas stream from the methanol synthesis is purified in a PSA unit to produce a purified hydrogen stream.

29. The method of claim 28, wherein a portion of the purified hydrogen stream is introduced to the methanol synthesis loop to adjust the SN of the feed gas stream.

30. The method of claim 21, wherein the SN is between 2.04 and 2.06.

31. The method of claim 21, wherein the methanol produced is between 1,000 and 20,000 metric tons/day.

32. The method of claim 21, wherein the acetic acid produced is between 300 and 6,000 metric tons/day.

33. The method of claim 21, wherein the reforming step uses a single train autothermal reformer.

34. The method of claim 21, further comprising:
providing at least a portion of the acetic acid produced to a vinyl acetate monomer (VAM) synthesis loop in an associated process;
combining the portion of the acetic acid with an ethylene source and oxygen to produce vinyl acetate monomer.

35. The method of claim 34, wherein the associated process uses the acetic acid as a reactant, uses the methanol product as a reactant, shares oxygen from a common air separation unit, shares common utilities, or a combination thereof.

36. The method of claim 34, wherein a CO2-rich stream is imported to the methanol synthesis loop from the VAM synthesis loop.

* * * * *